(12) United States Patent
Cone

(10) Patent No.: US 6,176,854 B1
(45) Date of Patent: Jan. 23, 2001

(54) PERCUTANEOUS LASER TREATMENT

(76) Inventor: Robert Roy Cone, 18672 Florida St., Huntington Beach, CA (US) 92648-1925

(*) Notice: Under 35 U.S.C. 154(b), the term of this patent shall be extended for 0 days.

(21) Appl. No.: 08/947,364

(22) Filed: Oct. 8, 1997

(Under 37 CFR 1.47)

(51) Int. Cl.⁷ .................................................... A61B 18/18
(52) U.S. Cl. ................................... 606/15; 606/9; 606/3; 606/10
(58) Field of Search .................. 606/7, 8, 9, 10, 606/14, 15, 16, 17

(56) References Cited

U.S. PATENT DOCUMENTS

| | | | |
|---|---|---|---|
| 5,000,752 | * 3/1991 | Hoskin et al. | 606/9 |
| 5,370,642 | * 12/1994 | Keller | 606/9 |
| 5,445,634 | * 8/1995 | Keller | 606/9 |
| 5,531,739 | 7/1996 | Trelles | 606/2.5 |

OTHER PUBLICATIONS

Apfelberg et al., Progress Report on Multicenter Study of Laser–Assisted Liposuction, 18 Aesth. Plast. Surg. 259–264 (1994).

Goldman et al., Cutaneous Laser Surgery 200–203 (Mosby 1994).

Ramirez et al., Endoscopic Plastic Surgery 28–35 (Springer 1996).

Bosniak, Ophthalmic Plastic and Reconstructive Surgery 617–625 (W.B. Saunders Company 1996).

Kohn, Textbook of Ophthalmic Plastic and Reconstructive Surgery 178–191 (Lea & Febiger 1988).

* cited by examiner

*Primary Examiner*—Linda C. M. Dvorak
*Assistant Examiner*—Sonya Harris-Ogugua
(74) *Attorney, Agent, or Firm*—Olson & Hierl, Ltd.

(57) ABSTRACT

A method of percutaneous and subcutaneous laser treatment of the tissue of a patient is provided. The tip of an optical fiber is passed through the skin, advanced through the tissue subcutaneously to a desired treatment area and withdrawn. Laser energy can be emitted at different levels during any or all of the skin penetration, advancement, tissue treatment and withdrawal phases. The present invention is useful for surgical treatments, and is especially suitable for minimally invasive plastic or cosmetic surgical and dermatological procedures without bleeding and with less edema, erythema and swelling and faster healing than conventional surface laser energy application, abrasion, scalpel surgery or chemical peel procedures.

36 Claims, No Drawings

PERCUTANEOUS LASER TREATMENT

TECHNICAL FIELD

The present invention relates to methods and procedures for the amelioration of cosmetic flaws and the like by the application of laser energy to a selected target region or site. The present invention is useful in the practice of surgery, especially plastic and cosmetic surgery, as well as dermatology. The present invention is especially suitable for minimally invasive surgical treatments in which a percutaneous approach is desired.

BACKGROUND OF THE INVENTION

Biological tissue comprises cells embedded in a primarily proteinaceous extracellular matrix. Collagen is one of the predominant proteins found in the extracellular matrix. Collagen can be altered by the application of thermal energy to become denatured and act as a biological glue. Thermal energy can also cause collagen fibers to become cross-linked, reducing the volume of the thermally treated collagen. The thermal effect may be conveniently produced by the interaction of laser generated light energy with tissue. Laser energy of the appropriate wavelength, energy and geometry can thus be used to weld together opposed tissue surfaces and shrink collagen-containing tissues.

The use of laser devices in various types of surgery is known. Such devices cause thermal coagulation and/or ablation of tissue by emission of a predetermined level of laser energy for a predetermined time. The unwanted tissue can be coagulated to the desired depth by laser energy at low energy density, or ablated by subjecting the tissue to a higher level of energy density. However, when laser energy is applied to the skin from an external source, erythema or sun-burning frequently occurs. The erythema can take weeks or months to subside, and discoloration or scarring of the skin may be a lasting result.

Several plastic surgery procedures involve the surgical removal of subcutaneous fat and excess skin and the tightening of the remaining skin. Such procedures include meloplasty (face lifts), eyebrow lifts and blepharoplasty for removal of bags under the eyes (dermochalasis and blepharochalasis). Beyer, C. K., Baggy lids, *Int. Ophthalmol. Clin.*, 10: 47–53 (1970). Traditional surgical approaches require cutting and removing excess skin and fat using incisions often centimeters in length. These approaches are subject to potential complications such as hemorrhage, hematoma, infection and removal of too much skin or fat (overcorrection). Kohn, R., *Textbook of Ophthalmic Plastic and Reconstructive Surgery*, pp. 177–191, 186, Lea & Febiger, Philadelphia (1988). As an example, surgical procedures for blepharoplasty are complex. Inappropriate or poorly performed surgery may result in an adverse cosmetic result, or may place the patient at risk for developing vision-threatening complications. Custer, P. L., Lower eyelid blepharoplasty, in Bosniak, S., editor, *Principles and Practice of Ophthalmic Plastic and Reconstructive Surgery*, pp. 617–625, 624, W. B. Saunders, Philadelphia (1996).

Lasers have been employed in cosmetic and reconstructive surgery. The Nd:YAG laser has been used to make incisions in the skin for face lifts (meloplasty) and for removal of bags under the eyes by blepharoplasty. Apfelberg, D. B., YAG laser meloplasty and blepharoplasty, *Aesth. Plast. Surg.* 19: 231–235 (1995). However, the Nd:YAG laser's continuous wave energy may be overly thermal and cause an excessively deep zone of penetration (about 4000 $\mu$m). The $CO_2$ laser has been employed in blepharoplasty using the transconjunctival approach. David, L. M., The laser approach to blepharoplasty, *J. Dermatol. Surg. Oncol.* 14: 741–235 (1988). While the use of laser energy has been reported to reduce bleeding during surgery and reduce pain during healing, a large incision is still required. Morrow, D. M., and Morrow, L. B., $CO_2$ laser blepharoplasty. A comparison with cold-steel surgery, *J. Dermatol. Surg. Oncol.*, 18: 307–313 (1992). The only advantage provided by the described laser technique was less swelling after surgery.

What is needed is a method of plastic surgery using a laser that provides more desirable tissue effects and which can also be used in a minimally invasive percutaneous approach.

SUMMARY OF THE INVENTION

A percutaneous method for the treatment of skin and subcutaneous tissue by means of a laser device capable of emitting pulses of light energy of an appropriate wavelength with relatively short pulse widths, at relatively low energy per pulse and relatively rapid pulse repetition rates is provided by the present invention. Light energy characterized by such parameters is applied subcutaneously to tissues underlying the skin. The method is useful for the practice of surgery, especially plastic and cosmetic surgery as well as dermatology. The method is non-invasive or minimally invasive and well suited for outpatient therapy. In particular, application of the laser energy directly to the tissue beneath the skin eliminates or reduces the erythema that can result when laser energy is applied to the skin from outside the body.

The method of the present invention is especially suitable for several procedures used in plastic and cosmetic surgery as well as dermatology. Procedures for which the method of the present invention can be used include, inter alia, the removal of pigmentation, such as lentigines (age spots), hyperpigmentation, lentigo (freckles), café-au-lait macules, actinic keratosis, melasma, and tattoos (body or facial). The method of the present invention can also be used for the removal of plantar warts, chin reshaping via the percutaneous laser melting or desiccation of fat, amelioration of turkey neck, and the treatment of some dilated blood vessels associated with rosacea. The method of the present invention is also suitable for coagulation of spider veins (<1 mm), removal of keloid scars, coagulation of varicose veins (>1 mm), reshaping of the upper lip, reshaping of the eyelids, permanent ablation of the hair follicle to permanently prevent hair regrowth and some types of otoplasty. The method of the present invention is also suitably used for the treatment of various cutaneous vascular lesions, such as port wine stains, hemangiomas, and telangiectasias, including those of the face and the leg.

The method of the present invention can also be used for plastic surgery treatments such as skin resurfacing, removal of perioral, periorbital and ear lobe wrinkles, treatment of nasal labial folds, perioral fat pads and marionette lines, lip lift, neck lift, eyebrow lift, lipolysis (of upper and lower eyelids, cheeks, abdomen, thighs), blepharoplasty, rhinoplasty, treatment of polly beak and internal weir (nostril reduction). Scars that can be treated using the method of the present invention include acne scars, keloids, chicken pox scars, stretch marks (striae), hypertrophic scars, and skin graft hypertrophy as well as pits and depressions. In addition, the method of the present invention is also suitable for burn debridement, and for the treatment of corns, papilloma (warts, condylomas, polyps) and skin cancer, including basal cell carcinoma.

A pulsed or continuous wave holmium:YAG laser, holmium:YSGG laser or other laser emitting light energy at a wavelength of about 1800 micrometers to about 2200 micrometers ("holmium laser") may be converted, in accordance with the present invention, to produce pulses of variable pulse-width at various energy levels. The light energy from a holmium laser has an ideal depth of penetration into tissue, about 250 to 400 $\mu$m. The holmium laser is a preferred light energy source because light energy obtained therefrom has the property of being able to cause cross-linking of collagen proteins, lysis of fat and bloodless incisions, primarily due to the wavelength of light emitted.

Energy from a relatively low power, short pulse-width, high repetition rate holmium laser, applied percutaneously through an optical fiber, can avoid burning or charring the tissue while accomplishing the desired beneficial physiologic effect. At lower energy densities, the collagen component of tissue can be cross linked, reducing its volume and causing shrinkage of the tissue. The holmium laser preferred for the practice of the present invention provides a marked advantage over earlier surgical techniques. Benefits of the holmium laser include less postoperative swelling, faster healing, no bleeding and no sutures to be removed. Additionally, the method of the present invention allows for the melting or desiccation of subcutaneous fat by the use of a relatively small diameter optical fiber, e.g. a 25–400 $\mu$m core diameter, that is introduced through the skin. The small diameter of the optical fiber, coupled with the low energy used, typically about 3 to 100 milliJoules per pulse (mJ/pulse), the narrow pulse-width, typically less than 100 microseconds ($\mu$S), and relatively fast repetition rate, generally 20 to 80 pulses per second (Hz), allow the fiber to penetrate the skin and be used subcutaneously upon tissue without perceptible charring as a result. Preferably, an energy level of about 3 mJ/pulse to about 20 mJ/pulse is used while the tip of the optical fiber is inserted through the skin. In comparison, most holmium lasers currently used in surgery are not stable in producing less than 500 mJ/pulse, typically have a pulse width of 300 to 350 $\mu$S and a repetition rate of 1 to 25 Hz.

The laser source typically comprises a housing containing the laser generating unit as well as optical and electronic control components therefor. The optical fiber is connected proximally to the light output of the laser and extends distally through a hand piece held by the surgeon. The light energy produced by the laser source is introduced into the proximal end portion of the optical fiber, which itself passes through a handpiece, and is emitted from the bare distal tip of the optical fiber distally to the target tissue. The tip of the optical fiber preferably has a core diameter of about 25 $\mu$m to 400 $\mu$m, more preferably about 50 $\mu$m to about 200 $\mu$m.

The face of the optical fiber tip is preferably aligned at a right angle to its longitudinal axis. Bleeding at the entry and exit point may be minimized by lasing at extremely low energy, as low as 1 mJ/pulse with a very short pulse width, preferably 10–30$\mu$S, during insertion through the skin or withdrawal of the optical fiber from the treatment site while exiting the skin.

The method aspect of the present invention includes a subcutaneous advancement phase as well as a withdrawal phase. In use, after penetration of the skin as described above, the tip of the optical fiber is moved forwardly through the tissue during the advancement phase. During this phase, the tip of the optical fiber is advanced through the tissue for the desired distance without emission of laser energy or with laser emission at a controlled power level chosen to achieve the effect desired. If desired, laser energy can be emitted from the tip during the advancement phase at a controlled energy level of less than about 3 to about 20 mJ/pulse, at a frequency of 20 to 80 Hz and a pulse width of 30 to 100 $\mu$S. A preferred energy emission frequency during the advancement phase is about 20 to 60 Hz. During advancement, very low emission energy of 3–10 mJ/pulse can be used to facilitate the advancement of the optical fiber and prevent tissue adherence to the optical fiber. If desired, laser energy to obtain a desired therapeutic effect can be emitted at an energy of 5 to 50 mJ/pulse.

The tip of the optical fiber may be maintained at the position of furthest advance and laser energy emitted there, or alternatively, the tip may be immediately withdrawn. During the period while the tip of the laser probe is being used to treat the tissue at a selected site, laser energy can be emitted at an energy of about 5 to about 50 mJ per pulse at a frequency of about 20 to about 60 Hz. During the withdrawal phase, laser energy can be emitted at about 5 to about 50 mJ/pulse at a frequency of about 20 to about 60 Hz, depending on the tissue effect desired, or at about 3 to about 10 mJ/pulse to prevent tissue adhering to the fiber during withdrawal. In other cases, the fiber can be withdrawn without using laser energy. The energy level can also be changed as the fiber moves from one area to another under the skin to obtain a desired effect. It is not necessary to remove the optical fiber, or to turn off the laser while the surgery is being performed.

In general, the level of light energy emitted during the withdrawal phase is equal to or greater than the emission level, if any, during the advancement phase. The power output, frequency and pulse-width may be varied as required to achieve the desired result, based on the surgeon's clinical experience.

DETAILED DESCRIPTION OF THE INVENTION

The method of the present invention initially produces a subcutaneous tunnel or cavity through the tissue as the tip of the optical fiber is moved forwardly during the advancement stage, or rearwardly during the withdrawal stage, usually while emitting light energy at a relatively low energy level and a relatively short pulse width. However, in some cases, for example, if extremely thin skin could be damaged by emitting light energy during advancement or withdrawal, the tip of the optical fiber can be advanced or withdrawn without emitting light energy.

The selected area can be treated by repeated advancement and withdrawal cycles of the tip of the optical fiber as appropriate. Each cycle can be directed at the same or a different radial angle. However, to avoid damage to blood vessels which can be situated substantially normal to the skin's surface, the optical fiber is moved unidirectionally rather than so as to sweep laterally through a sector like a windshield wiper. Advancement and withdrawal cycles are repeated as appropriate through other openings within the selected region, until the entire region has been treated.

Tissue can be removed or affected by several processes, including vaporization; cross linkage, which produces shrinkage; disruption of cellular membranes; desiccation of fat cells; lipolysis or melting of fat cells; melting and fusion of tissue components (welding) and denaturation or coagulation of proteins. Little bleeding occurs during such processes due to the hemostasis produced by the effects of the applied light energy. The effects produced depend on the wavelength and energy level used. The process of tissue ablation requires relatively higher energy levels. Tissue welding may be used to join opposed tissue surfaces at relatively low energy levels, without the need for sutures and their subsequent removal.

Blood and tissue coagulation is produced by heating the tissue to at least about 62 degrees Celsius. Tissue vaporization or ablation is produced by heating the tissue to at least about 100 degrees Celsius, causing the water in the cells to turn into steam. The small volume of steam produced is rapidly cooled by interaction with the tissue, and quickly condenses. Tissue disruption may also be caused by attendant concurrent acoustic effects of laser energy emission.

The physiological response of the treated area progresses through a continuum of at least three phases of wound healing after superficial or percutaneous laser treatment. First, there is an edema phase, seen in many cases within about 10 days after treatment. The sequence of events generally follows a course including two days of swelling and two days of subsidence. Usually swelling is less pronounced after treatment with a holmium laser than after treatment with a $CO_2$ laser. The second phase is characterized by the proliferation of fibroblasts. The third phase is the resolution phase in which tissue remodeling takes place.

The tissue in the region to be treated subcutaneously is preferably hydrated before laser treatment by the injection of water or an aqueous saline solution. The water or aqueous saline solution used for this purpose may include an acceptable local anesthetic. The overall treatment parameters of energy levels, pulse width and frequency typically used in illustrative procedures are tabulated in Table 1, below.

In each case, for penetration of the skin, the optical fiber was positioned perpendicular to the skin, and a very low level of light energy was emitted while very gentle pressure was applied. Typical parameters used for skin penetration were 3–10 mJ/pulse, preferably about 5 mJ/pulse, frequency of about 20–60 Hz and pulse width of about 40–80 $\mu S$, although skin penetration of the fiber optic can also be achieved using lower or higher energies.

Similar energy parameters may be used to prevent or minimize tissue adherence while advancing the fiber to the treatment site or withdrawing the fiber from the treatment site. The preferred energy parameters for treatment at the site or along a tissue track, are set forth in Table 1.

TABLE 1

Preferred Parameters for Holmium Laser Treatment in Selected Procedures

| PROCEDURE | FREQUENCY Hz | ENERGY mJ/Pulse | PULSE WIDTH ($\mu S$) |
|---|---|---|---|
| Upper Blepharoplasty | 20–60 | 5–40 | 50–80 |
| Lower Blepharoplasty | 20–60 | 5–40 | 40–70 |
| Vein Coagulation | 20–60 | 5–40 | 70–90 |
| Skin Wrinkle Removal | 20–60 | 5–40 | 40–70 |
| Telangiectasia | 20–60 | 5–20 | 40–100 |

The laser tissue effect on the selected tissue site can be controlled by modulating the energy per pulse, repetition rate and/or pulse width of the emitted laser energy.

EXAMPLE 1

Percutaneous Localized Treatment Parallel to the Skin Surface

The areas selected for treatment were first hydrated by an injection of water, an aqueous saline solution, or, preferably, an aqueous saline solution containing an appropriate local anesthetic. The injected liquid served to absorb excess light energy and heat to cool the tissue, and to provide a buffer zone, which is especially useful in some locations, such as around the eyes.

The tip of the optical fiber was placed on the skin surface, at about a 90 degree angle to the skin surface. The optical fiber was a bare optical fiber of about 100 $\mu m$ to about 365 $\mu m$ in core diameter, preferably about 200 $\mu m$ core diameter. The tip pierced the skin and was advanced into the subcutaneous tissue while emitting laser energy at about 5 mJ/pulse, a pulse width of about 40 to about 70 $\mu S$ at a frequency of about 20 to about 60 Hz. Low energies were used to minimize adverse thermal effects to the skin, such as scarring, depigmentation or hyperpigmentation, at the site of entry.

After insertion of the tip of the optical fiber though the skin, the fiber was turned so that it was roughly parallel to the plane of the skin surface. The fiber was advanced and withdrawn repeatedly as needed to treat the selected region. Energy emission was increased after the initial advancement stage to a therapeutic level of about 5 to about 50 mJ/pulse, depending on the diameter of the fiber, smaller fibers requiring less energy. Preferably, about 20 mJ/pulse was used at about the same pulse width and frequency. The optical fiber was moved axially to and from, but not swept laterally like a windshield wiper. The treatment of a selected area continued until audible cavitation sounds ("popping") ceased. Such cavitation sounds signalled the destruction of the fat present at the site (lipolysis) and the heating of the collagen. The optical fiber was then withdrawn from the skin, while continuing to emit energy at or below the therapeutic level, in order to minimize the amount of tissue adhering to the tip of the optical fiber.

This method has been used when the primary objective is the removal of fat or the coagulation of blood vessels, with a secondary objective of tightening the skin. This method is appropriate, for example, for lipolysis of the fat pads and tightening (blepharoplasty) of the upper and lower eyelids, removal of nasal labial folds, removal of perioral and periorbital wrinkles; treatment of marionette lines and wrinkles of the ear lobes; neck lifts and lip lifts. This method may also be used for coagulation of telangiectasias, varicose and spider veins, hemangiomas and rosacea.

EXAMPLE 2

Percutaneous Localized Treatment Non-parallel to Skin Surface

The method of Example 1 was used with the modification that the optical fiber was directed to the treatment site or used along a treatment track that was not parallel to the plane of the skin surface. This method is appropriate, for example, for the treatment of polly beak, wherein the shape of the nose is lifted and reshaped as desired by producing tissue shrinkage combined with lipolysis. For this purpose, the frequency used was about 20 to about 60 Hz; all other parameters were the same as used in Example 1. This method is useful when the primary objective is the removal of fat or removal of excess vascularization, with a secondary objective of tissue shrinkage to tighten the skin.

EXAMPLE 3

Tattoo Removal

Tattoo removal is accomplished by inserting the tip of the optical fiber through the skin in the pigmented area, at the fiber penetration energy parameters as described above, keeping the optical fiber perpendicular to the skin or tilting it at an angle substantially parallel to the skin and advancing and withdrawing the optical fiber while emitting energy at the parameters as described in Example 1. Subsequent additional penetrations are made until the entire pigmented area is treated.

EXAMPLE 4

Incision (Internal Weir)

A bare optical fiber about 365 μm in diameter was inserted at the base of the nostril. The method of Example 1 was used to create a wedge-shaped opening or channel; the parameters were: about 10 to about 50 mJ/pulse, preferably about 20 mJ/pulse, pulse width 50–70 μS and frequency about 60 Hz. The edges of the channel were sutured together to reduce the size of the nostril opening.

EXAMPLE 5

Cartilage Vaporization, Bone Reduction

This method is useful for rhinoplasty (commonly referred to as a nose job), which can be performed without postoperative bruising and black eyes. A series of holes are made through the skin and through cartilaginous and bony tissue using the optical fiber. The holes are placed at or around the nose ridge protrusion in a configuration like the perforations at the edges of a postage stamp. During the entry phase, the tip of the 200 or 365 μm bare optical fiber is placed at a 90 degree angle relative to the skin. Low energies (about 5 mJ/pulse), are used to minimize adverse thermal effects on the skin at the entrance point of the optical fiber.

Therapy is administered by advancing the fiber internally through cartilaginous and/or bony tissue. Energy parameters for therapy are 15–40 mJ/pulse, 40–70 μS pulse width, at 20–60 Hz. After the "postage stamp" configuration is completed, external pressure is applied to the "postage stamp" to dislocate it from its original structural connections. The cartilaginous/bone fragment may be left in the body to be naturally absorbed over time.

EXAMPLE 6

Coagulation of Varicose Veins

This method is useful for treatment of varicose veins. The area surrounding the veins to be treated was anesthetized. The optical fiber, preferably a bare optical fiber, about 200 μm to about 365 μm in diameter, was placed on the skin above one end of the visible portion of the vein to be treated. The optical fiber penetrated the surface of skin at about a 90 degree angle and entered the vein, using parameters of about 5 mJ/pulse, 50–90 μS pulse width and 20–60 Hz. The energy was increased to about 5–25 mJ/pulse, preferably about 15 mJ/pulse, with the optical fiber tip within the vein. Treatment was continued until the vein was coagulated. After the treatment, the tip of the optical fiber was withdrawn while lasing at the therapeutic parameters, i.e. about 5–25 mJ/pulse, preferably about 15 mJ/pulse, 50–90 μS pulse width and 20–60 Hz. The treatment was repeated at the other end of the visible portion of the varicose vein.

The foregoing is intended to be illustrative of the present invention, but not limiting. Numerous variations and modifications of treatment parameters and energy sources may be utilized without departing from the spirit and scope of this invention.

What is claimed is:

1. A method for percutaneous laser treatment of a patient having a condition requiring treatment, comprising the steps of:
   selecting an area to be treated;
   selecting a source of holmium laser energy capable of stable energy emission of less than about 500 milliJoules per pulse;
   selecting an optical fiber of appropriate core diameter said optical fiber having a tip;
   inserting the tip of the optical fiber through the patient's skin into tissue;
   advancing the tip of the optical fiber through the tissue;
   treating the tissue by emitting the holmium laser energy through the tip of the optical fiber at an energy level less than about 200 milliJoules per pulse, with a pulse width less than about 200 microseconds and at an energy emission frequency of greater than about 5 Hertz while treating the tissue; and
   withdrawing the tip of the optical fiber through the tissue.

2. The method of claim 1, further comprising the step of emitting the holmium laser energy through the tip of the optical fiber at an energy level less than about 200 milliJoules per pulse, with a pulse width less than about 200 microseconds and at an energy emission frequency of greater than about 5 Hertz while advancing the tip of the optical fiber.

3. The method of claim 2 wherein the pulsed holmium laser energy is emitted through the tip of the optical fiber at a selected energy level less than about 100 milliJoules per pulse, with a pulse width less than 100 microseconds and at an energy emission frequency greater than about 20 Hertz while the tip of the optical fiber is advanced through the tissue.

4. The method of claim 2 wherein the energy emission frequency while the tip of the optical fiber is advanced through tissue is about 20 to about 80 Hertz.

5. The method of claim 2 wherein the energy emission level while the tip of the optical fiber is advanced through tissue is about 5 milliJoules per pulse to about 50 milliJoules per pulse.

6. The method of claim 2 wherein the energy emission frequency while the tip of the optical fiber is advanced through tissue is about 20 to 80 Hertz.

7. The method of claim 1, further comprising the step of emitting the holmium laser energy through the tip of the optical fiber at an energy level less than about 200 milliJoules per pulse, with a pulse width less than about 200 microseconds and at an energy emission frequency of greater than about 5 Hertz while withdrawing the tip of the optical fiber.

8. The method of claim 7 wherein the energy emission level while the tip of the optical fiber is withdrawn through tissue is about 5 milliJoules per pulse to about 50 milliJoules per pulse.

9. The method of claim 7 wherein the energy emission frequency while the tip of the optical fiber is withdrawn through tissue is about 20 to about 80 Hertz.

10. The method of claim 1 further comprising the step of emitting light energy from the tip of the optical fiber while the tip of the optical fiber is inserted through the skin at an energy level of about 3 milliJoules per pulse to about 20 milliJoules per pulse.

11. The method of claim 10 wherein the energy emission frequency while the tip of the optical fiber is inserted through the skin is about 20 to 80 Hertz.

12. The method of claim 1 wherein the energy emission level while the tip of the optical fiber is advanced through the tissue is about 3 milliJoules per pulse to about 20 milliJoules per pulse.

13. The method of claim 1 wherein the pulse width is 5 to 100 microseconds.

14. The method of claim 1 wherein the tissue is skin tissue.

15. The method of claim 1 wherein the tissue is tissue underlying the skin.

16. The method of claim 1 wherein the condition requiring treatment is blepharochalasis.

17. The method of claim 1 wherein the condition requiring treatment is dermochalasis.

18. The method of claim 1 wherein the condition requiring treatment is turkey neck.

19. The method of claim 1 wherein the condition requiring treatment is rosacea.

20. The method of claim 1 wherein the condition requiring treatment is plantar warts.

21. The method of claim 1 wherein the condition requiring treatment is keloid scars.

22. The method of claim 1 wherein the condition requiring treatment is telangiectasia.

23. The method of claim 1 wherein the condition requiring treatment is wrinkles.

24. The method of claim 1 wherein the condition to be treated is unwanted hair follicles.

25. The method of claim 1 wherein the condition to be treated is the pigmented area of a tattoo.

26. The method of claim 1 wherein the condition requiring treatment is marionette lines.

27. The method of claim 1 wherein the condition requiring treatment is basal cell carcinoma.

28. The method of claim 1 wherein the condition requiring treatment is acne scars.

29. The method of claim 1 wherein the condition requiring treatment is chicken pox scars.

30. The method of claim 1 wherein the condition requiring treatment is age spots.

31. The method of claim 1 wherein the condition requiring treatment is hemangioma.

32. The method of claim 1 wherein the condition requiring treatment is port wine stains.

33. The method of claim 1 wherein the condition requiring treatment is hyperpigmentation.

34. The method of claim 1 wherein the condition requiring treatment is varicose veins.

35. The method of claim 1 wherein the condition requiring treatment is polly beak.

36. The method of claim 1, wherein emitting the holmium laser energy occurs while advancing and withdrawing the tip.

* * * * *